United States Patent [19]

Mills

[11] 4,301,206
[45] Nov. 17, 1981

[54] SURGICAL WRAPPER

[76] Inventor: James S. Mills, 500 N. Green Bay Rd., Lake Forest, Ill. 60045

[21] Appl. No.: 92,546

[22] Filed: Nov. 8, 1979

[51] Int. Cl.³ ............................................. B32B 23/02
[52] U.S. Cl. .................................. 428/193; 112/441; 428/192; 428/224; 428/245
[58] Field of Search .............. 428/192, 193, 224, 247, 428/245, 102; 112/137, 138, 418, 423, 441

[56] References Cited

U.S. PATENT DOCUMENTS

| | | | |
|---|---|---|---|
| 1,191,707 | 7/1916 | Kimmel | 112/137 |
| 1,227,076 | 5/1917 | Rubinstein | 112/137 |
| 1,969,950 | 8/1934 | Seaman | 112/137 |
| 2,124,714 | 7/1938 | Rosenberg | 112/137 |
| 2,753,597 | 7/1956 | Bird et al. | 428/192 |
| 2,766,504 | 10/1956 | Beeby | 428/192 |
| 3,316,117 | 4/1967 | Clifford et al. | 428/193 |
| 3,791,324 | 2/1974 | Shulman | 112/138 |
| 3,862,876 | 1/1975 | Graves | 428/193 |
| 4,154,884 | 5/1979 | Jentschmann | 428/193 |
| 4,190,010 | 2/1980 | Bibby | 428/193 |

*Primary Examiner*—James J. Bell
*Attorney, Agent, or Firm*—James T. FitzGibbon

[57] ABSTRACT

A surgical wrapper is provided which minimizes the problems of raw edges, linting, and pinholes. A woven binding or tape is positioned about the outer edge of a woven material of predetermined size that has opposing major surfaces. The woven tape has a predetermined length and width, and includes a first segment which is juxtaposed to one of the major surfaces of the woven material along a marginal portion of the woven material. The tape is folded lengthwise about the outer edge of the woven material, and has a second segment which is juxtaposed to the outer major surface of the woven material along a marginal portion of the woven material. The first segment and second segment of the tape are secured to the woven material, as by means of thread.

1 Claim, 3 Drawing Figures

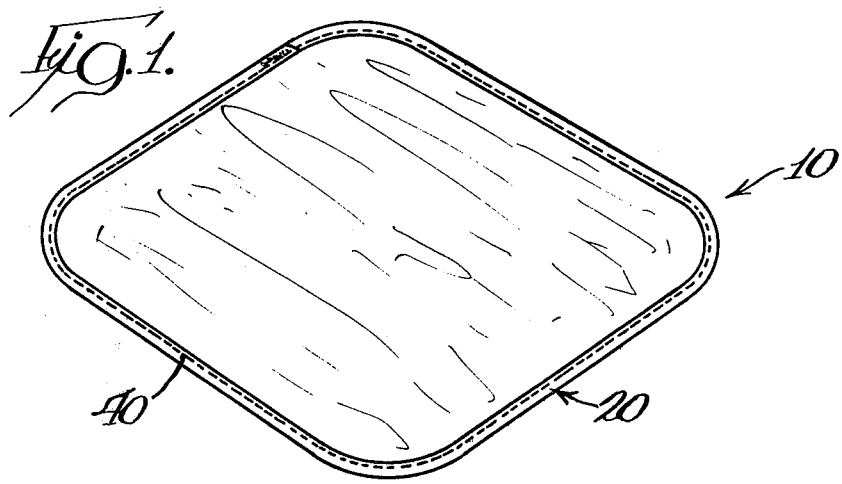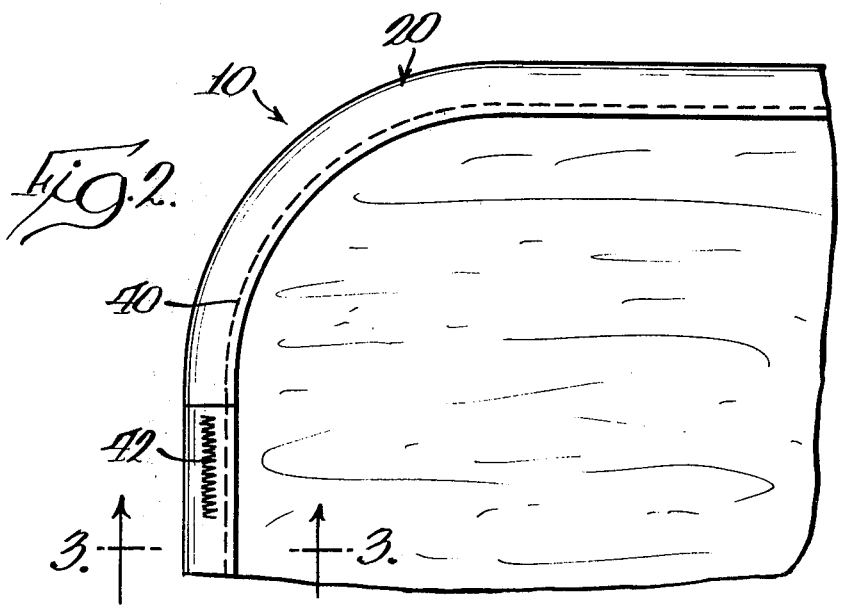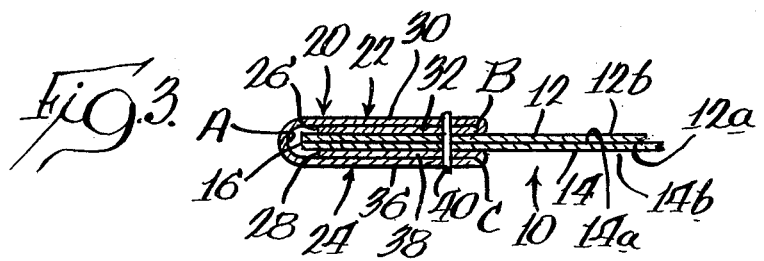

SURGICAL WRAPPER

DESCRIPTION

Technical Field of Invention

The present invention relates to surgical wrappers and, more particularly, to surgical wrappers having a binding or tape along the outer edge.

Background of the Invention

Conventional surgical wrappers have been comprised of a single layer of woven material which is used, among other things, for wrapping surgical instruments. The instruments are packed in the surgical wrapper, the instruments together with the surgical wrapper are sterilized, and are then made available to a physician when desired. The surgical wrappers are laundered and are intended for repeated use.

A problem with surgical wrappers that are a single layer is that the edges become raw and unraveled which results in undersirable lint that may accumulate on the surgical instruments. In addition, pinholes occur in the woven fabric. As a result, the life of the product is limited and possible dangers may even be posed by a lack of sterility from using a surgical wrapper that has holes or frayed edges.

An attempt at overcoming these problems has been to overlap two layers of woven material and secure these layers together about their outer edge by means of thread. The thread lessens the problem of the edges unraveling but does not eliminate it, because portions of the edge of the woven material remain exposed, become raw or unraveled, and present the problem of linting.

SUMMARY OF THE INVENTION

The foregoing disadvantages of the prior art are overcome by the present invention in which a binding or tape is folded over the outer edge of a woven material of predetermined size. The tape has a predetermined length and width and includes a first segment that is juxtaposed to one of the major surfaces of the woven material along a marginal portion of the woven material. The tape has a second segment on the opposite side of the fold line, and a second segment is juxtaposed to the other major surface of the woven material along a marginal portion of the woven material.

The first and second segments of the tape are secured to the woven material, as by a thread that extends through the woven material and the first and second segments of the tape.

BRIEF DESCRIPTION OF THE DRAWING

FIG. 1 is a perspective view of the surgical wrapper of the present invention;

FIG. 2 shows a portion of the surgical wrapper of FIG. 1 on an enlarged scale; and FIG. 3 is a cross-sectional view taken along line 3—3 in FIG. 2.

DESCRIPTION OF THE PREFERRED EMBODIMENT

While this invention is susceptible of embodiment in many different forms, there is shown in the drawing and described herein a detail a preferred embodiment of the invention, with the understanding that the present disclosure is to be considered as an exemplification of the principles of the invention and is not intended to limit the invention to the embodiment illustrated. The scope of the invention is pointed out in the appended claims.

Referring to the drawing, the surgical wrapper 10 of the present invention has two overlapping layers 12 and 14 of woven material (FIG. 3). The layers of woven material preferably are coextensive, have generally the same dimensions, and define an outer edge 16 along their perimeter. Each of the layers 12 and 14 of woven material has an inner surface 12a and 14a, respectively, juxtaposed to the inner surface of the other layer. The layers also have an outer surface 12b and 14b, respectively, each of which defines an outer surface of the surgical wrapper 10. Each of the layers of woven material has a marginal portion adjacent to the outer edge 16.

As shown in FIGS. 1-3, the surgical wrapper also includes a woven ribbon, binding or tape 20 that has a predetermined length and width and extends along the entire length of the marginal portion of the layers 12 and 14. The tape 20 is folded lengthwise about the outer edge 16 of the layers 12 and 14 along a first fold line A, as shown in FIG. 3. Fold line A is spaced outwardly from the outer edge 16 of each layer of woven material.

The tape includes a first segment 22 on one side of the fold line A and a second segment 24 on the other side of fold line A.

The first segment 22 extends between the first fold line A and the longitudinal edge 26 of the tape, and the second segment 24 extends between the first fold line A and the other longitudinal edge 28 of the tape.

The first segment 22 overlies the outer surface of one of the layers, such as layer 12, along a marginal portion of layer 12. The second segment 24 overlies the outer surface of the other layer, such as layer 14, along a marginal portion of layer 14.

As depicted in FIG. 3, the first segment 22 of the tape is folded inwardly upon itself, lengthwise, along a second fold line B. The first segment of the tape thereby includes a first portion 30 that is defined between the first fold line A and the second fold line B, and a second portion 32 that is defined between the second fold line B and the longitudinal edge 26 of the tape.

The second portion 32 has a smaller transverse dimension than the first portion 30 and is positioned between the first portion and the outer surface 12b of the layer 12; the second portion has one surface juxtaposed to a surface of the first portion and an opposite surface that is juxtaposed to the outer surface 12b of the layer 12.

The second segment 24 is folded inwardly upon itself, lengthwise, along fold line C. The second segment 24 of the tape includes a first part 34 disposed between the fold line A and the fold line C, and a second part 38 positioned between the fold line C and the longitudinal edge 28 of the tape. Part 38 of the tape has a smaller transverse dimension than part 36, and is positioned between the first part 36 and the outer surface 14b of layer 14. Part 38 has one surface juxtaposed to a surface of part 36, and an opposite surface juxtaposed to the outer surface 14b of the layer 14.

Thus, as shown in FIG. 3, the tape 20 includes portion 30 which overlies and is in surface-to-surface contact with portion 32, portion 32 which overlies and is in surface-to-surface contact with layer 12 of the surgical wrapper, part 36 which overlies and is in surface-to-surface contact with part 38, part 38 which overlies and is in surface-to-surface contact with layer 14 of the surgical wrapper, and layers 12 and 14 of the surgical wrapper overlie one another and are in surface-to-surface contact.

As depicted in FIG. 3, means such as thread 40 is used for securing the tape 20 to the layers 12 and 14 of the surgical wrapper. The thread extends through portions 30 and 32 of the tape, as well as parts 36 and 38 of the tape and layers 12 and 14 of the surgical wrapper. The thread 40 thereby secures the tape 20 and the two layers 12 and 14 together along the marginal portions of the layers.

In the resulting structure, the outer edge 16 of the layers 12 and 14 is covered by the tape 20 which is folded about line A, and the securement of the tape to the layers 12 and 14 by means of thread 40 insures that a marginal portion of the layers 12 and 14 is enveloped by the tape 20, thereby preventing the edge 16 and/or the marginal portion of the layers 12 and 14 from fraying or unraveling. As shown in FIGS. 1-3, it is preferable to have the thread 40 extending through the tape closer to the inner portion of the tape adjacent to lines B and C, rather than the outermost portion of the tape which would be near line A. This reduces the tendency for the portions of the tape positioned inwardly of thread 40 from causing stress to the thread which might cause the thread to tear.

A straight stitch may be used for sewing together the tape and the layers 12 and 14 of the surgical wrapper. As illustrated in FIGS. 1 and 2, the tape 20 extends around the entire periphery of the layers 12 and 14, and one end of the tape overlaps the other end of the tape. A zig-zag stitch may be used with thread 42 to provide a strong securement along the overlapping portions of the tape, with the thread 42 extending through both of the overlapping ends of the tape as well as the layers 12 and 14.

By way of example, the surgical wrapper may be generally square, having sides 18 inches long, with curved corners having a radius of curvature of about 1-½ inches. The width of the tape is 1-⅛ inches with the first portion and the first part of the tape each being approximately 5/16 inch and covering a marginal portion of the surgical wrapper about 5/16 inch wide. The second portion and the second part of the tape are each about ¼ inch, the stitching of the thread is approximately 1/16 inch from fold lines B and C, and approximately ¼ inch from fold line A and the outer edge of the layers of the surgical wrapper, and approximately 3/16 inch from the longitudinal edges of the tape. The woven material is two overlapping layers, each of which is a tightly woven blend of 50% combed cotton and 50% polyester.

As can be seen from the foregoing, the present invention provides a surgical wrapper having a construction which minimizes pinholes and the amount of undesirable linting that will occur. The wrappers can be provided in different sizes, and the color of the tape can be different for each size, so that the sizes will be color-coded.

What is claimed is:

1. A surgical wrapper comprising:
two overlapping layers of woven material, wherein each layer of woven material has generally the same dimensions, each layer has an inner surface juxtaposed to the inner surface of the other layer, and an outer surface that defines an outer surface of said surgical wrapper, and each layer has an outer edge along its perimeter, woven tape means is folded lengthwise about said outer edge of said layers along a first fold line and has a first segment overlying the outer surface of one of said layers along a marginal portion of said one layer and a second segment overlying the outer surface of the other of said layers along a marginal portion of said other layer, and said first tape segment extends between said first fold line and one longitudinal edge of said tape means and said second tape segment extends between said first fold line and the other longitudinal edge of said tape segment, said first segment is folded inwardly upon itself lengthwise along a second fold line to define a first portion between said first and second fold lines, and a second portion between said second fold line and said one longitudinal edge of said tape segment, said second portion has a smaller transverse dimension than said first portion and is positioned between said first portion and said outer surface of said one layer, said second segment is folded inwardly upon itself lengthwise along a third fold line to define a first part between said first and third fold lines, and a second part between said third fold line and the other longitudinal edge of said tape segment, said second part has a smaller transverse dimension than said first part and is positioned between said first part and said outer surface of said other layer, thread means for securing said tape means to said layers, said thread means extending through said two layers, said first portion and said second portion of said first segment of said tape means, and said first part and said second part of said second segment of said tape means for securing the tape means and the two layers together along said marginal portion of said layers while covering said outer edge of said layers, said thread means being positioned closer to said second and third fold than said first fold, and said thread means being positioned closer to said second and third fold than said first fold, said tape means extends along the entire length of said marginal portion of said layers.

* * * * *

REEXAMINATION CERTIFICATE (282nd)

United States Patent [19]

Mills

[11] B1 4,301,206

[45] Certificate Issued   Dec. 4, 1984

[54] SURGICAL WRAPPER

[75] Inventor: James S. Mills, Lake Forest, Ill.

[73] Assignee: Medline Industries, Inc.

Reexamination Request:
No. 90/000,473, Nov. 25, 1983

Reexamination Certificate for:
Patent No.: 4,301,206
Issued: Nov. 17, 1981
Appl. No.: 92,546
Filed: Nov. 8, 1979

[51] Int. Cl.³ .............................................. B32B 23/02
[52] U.S. Cl. ................................. 428/193; 112/441;
428/192; 428/224; 428/245

[56] References Cited

U.S. PATENT DOCUMENTS

| | | | |
|---|---|---|---|
| 1,191,707 | 7/1916 | Kimmel | 112/137 |
| 1,207,977 | 12/1916 | Moffatt. | |
| 1,227,076 | 8/1917 | Rubinstein | 112/137 |
| 1,230,906 | 6/1917 | Krug et al.. | |
| 1,237,801 | 8/1917 | Moffatt | 112/138 |
| 1,562,446 | 11/1925 | Ham. | |
| 1,969,950 | 8/1934 | Seaman | 112/137 |
| 2,026,484 | 12/1935 | Sailer | 112/138 |
| 2,124,714 | 7/1938 | Rosenberg | 112/137 |
| 2,347,145 | 4/1944 | Ackerman | 112/138 |
| 2,753,597 | 7/1956 | Bird et al. | 428/192 |
| 2,766,504 | 10/1956 | Beeby | 28/72 |
| 3,134,347 | 5/1964 | Seaman | 112/140 |
| 3,316,117 | 4/1967 | Clifford et al. | 428/193 |
| 3,791,324 | 2/1974 | Shulman | 112/138 |
| 3,862,876 | 1/1976 | Graves | 428/193 |
| 4,128,066 | 12/1978 | Peloggio | 112/27 |
| 4,154,884 | 5/1979 | Jentschmann | 428/193 |
| 4,190,010 | 2/1980 | Bibby | 112/419 |
| 4,280,421 | 7/1981 | Price | 112/147 |

OTHER PUBLICATIONS

*Bobbin,* Oct. 1976, p. 30.
*Stitches, Seams and Stitchings,* Jan. 25, 1965, Federal Standard No. 751a, Seam Type BSc-1.

Primary Examiner—James J. Bell

[57]   ABSTRACT

A surgical wrapper is provided which minimizes the problems of raw edges, linting, and pinholes. A woven binding or tape is positioned about the outer edge of a woven material of predetermined size that has opposing major surfaces. The woven tape has a predetermined length and width, and includes a first segment which is juxtaposed to one of the major surfaces of the woven material along a marginal portion of the woven material. The tape is folded lengthwise about the outer edge of the woven material, and has a second segment which is juxtaposed to the outer major surface of the woven material along a marginal portion of the woven material. The first segment and second segment of the tape are secured to the woven material, as by means of thread.

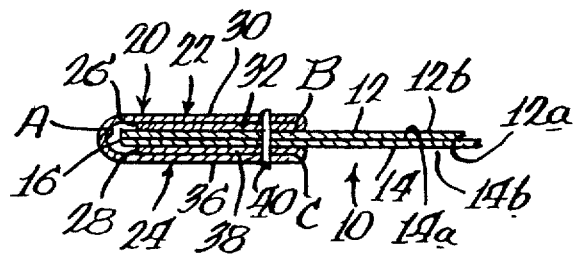

REEXAMINATION CERTIFICATE ISSUED UNDER 35 U.S.C. 307.

THE PATENT IS HEREBY AMENDED AS INDICATED BELOW.

AS A RESULT OF REEXAMINATION, IT HAS BEEN DETERMINED THAT:

Claim 1 is cancelled.

* * * * *